United States Patent
Namba et al.

(10) Patent No.: US 6,980,294 B2
(45) Date of Patent: Dec. 27, 2005

(54) BIOMOLECULE ANALYZER

(75) Inventors: Akihiro Namba, Tokyo (JP);
Kiyochika Ishibashi, Hachioji (JP);
Yoshiaki Horikawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/017,506

(22) Filed: Dec. 20, 2004

(65) Prior Publication Data

US 2005/0213090 A1    Sep. 29, 2005

Related U.S. Application Data

(63) Continuation of application No. PCT/JP03/07894, filed on Jun. 20, 2003.

(30) Foreign Application Priority Data

Jun. 21, 2002 (JP) .............................. 2002-181928
Dec. 12, 2002 (JP) .............................. 2002-361158

(51) Int. Cl.[7] .......................................... G01N 21/64
(52) U.S. Cl. .................................. 356/318; 250/458.1
(58) Field of Search .............................. 356/317, 318, 356/417; 250/458.1, 459.1, 461.1, 461.2

(56) References Cited

U.S. PATENT DOCUMENTS 5,706,083 A * 1/1998 Iida et al. .................... 356/328

FOREIGN PATENT DOCUMENTS

| JP | 3-72244 | 3/1991 |
|---|---|---|
| JP | 7-199079 | 8/1995 |
| JP | 7-333516 | 12/1995 |
| JP | 11-38324 | 2/1999 |
| JP | 2000-275529 | 10/2000 |
| JP | 2001-194305 | 7/2001 |
| WO | WO 01/44817 A2 | 6/2001 |

* cited by examiner

Primary Examiner—F. L. Evans
(74) Attorney, Agent, or Firm—Scully, Scott, Murphy & Presser

(57) ABSTRACT

A biomolecule analyzer of the present invention analyzes dynamic behaviors of biomolecules, and comprises image obtaining means for obtaining an image corresponding to at least one observation area of a biological sample containing biomolecules held in a measurable state, designation means for designating an arbitrary point on the image obtained by the image obtaining means, arrangement means for arranging a measuring point in a point position on the sample corresponding to the point designated by the designation means so that the measuring point may continuously coincide with the point position, measurement means for measuring a signal derived from dynamic information of an object to be measured from the measuring point arranged by the arrangement means, and analysis means for analyzing measuring results of the measurement means.

6 Claims, 6 Drawing Sheets

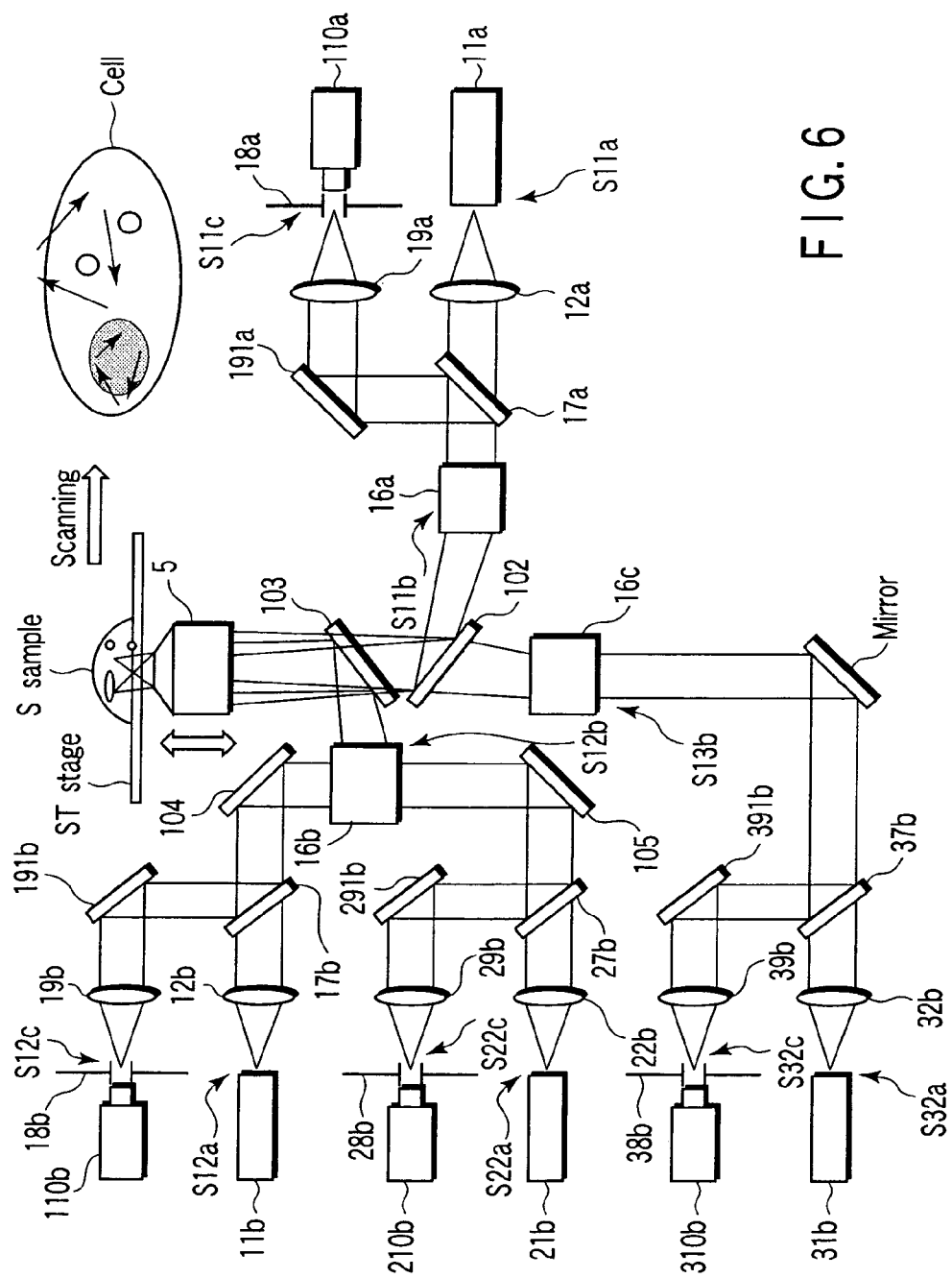
F I G. 6

BIOMOLECULE ANALYZER

CROSS REFERENCE TO RELATED APPLICATIONS

This is a Continuation Application of PCT Application No. PCT/JP03/07894, filed Jun. 20, 2003, which was published under PCT Article 21(2) in Japanese.

This application is based upon and claims the benefit of priority from prior Japanese Patent Applications No. 2002-181928, filed Jun. 21, 2002; and No. 2002-361158, filed Dec. 12, 2002, the entire contents of both of which are incorporated herein by reference.

BACKGROUND OF THE INVENTION

1. Field of the Invention

The present invention relates to a biomolecule analyzer which obtains statistical properties of a plurality of specific portions of a sample and an interaction between the portions.

2. Description of the Related Art

Concerning a confocal scanning type optical microscope, for example, there is an explanation in a document "Confocal Microscopy" T. Wilson (ed.) Academic press (London). As an explanation which mainly targets a biological sample, there is a document "Handbook of Biological confocal Microscopy" J. B. Pawley (ed.) Plenum Press (New York) or the like. Concerning fluorescent correlation spectroscopy, for example, there is an explanation in a document "Fluorescence correlation spectroscopy" R. Rigler, E. S. Elson (eds.) Springer (Berlin) or the like.

In the 1990s, there has been a rapid increase in studies on single molecule detection/imaging which uses fluorescence. For example, as single molecule detection methods, a document P. M. Goodwin etc. ACC. Chem. Res. (1996), Vol. 29, p 607 to 613, fluorescent correlation spectroscopy (FCS), and the like can be cited. According to the fluorescent correlation spectroscopy, fluorescence-labeled proteins or carrier particles are suspended in a solution within a visual field of a confocal laser microscope, a fluctuation in fluorescence intensity based on Brownian motion of such fine particles is analyzed to obtain an auto-correlation function, and the number, sizes or the like of target fine particles is estimated. For example, this technology is discussed in PCT National Publication No. 11-502608 or "Protein nucleic acid enzyme" by Masataka Kinjo, Vol. 44, No. 9, p 1431 to 1437 (1999).

Meanwhile, concerning the confocal scanning type microscope and the fluorescent correlation spectroscopy, some patent applications have been filed. For example, according to Jpn. Pat. Appln. KOKAI Publication No. 2001-194303, a laser beam is guided to a cylindrical lens, and an exciting light beam in a line shape which is not a spot light is accordingly generated to illuminate a sample. This lineshaped light beam is subjected to light scanning by a galvanometer mirror to move in a vertical direction of the cylindrical lens, thereby exciting the entire portion in an imaging area of the sample two-dimensionally. A fluorescent signal from the sample is converted into an image by a two-dimensional photodetector such as a CCD. By this method, molecules only of a translational diffusion speed lower than a scanning speed of the cylindrical lens are excited to display fluorescence on the image.

Additionally, according to Jpn. Pat. Appln. KOKAI Publication No. 08-43739 and Jpn. Pat. Appln. KOKAI Publication No. 2000-98245, at a scanning type optical microscope, fluorescence from a multiple-dyed sample is subjected to spectroscopy through a grating or a prism, and detected for each component wavelength by a plurality of photodetectors.

According to Jpn. Pat. Appln. KOKAI Publication No. 08-068694, fluorescent correlation analysis is carried out from a spatially separated portion by entering an optical fiber into a reaction container which receives a liquid sample. It is disclosed that one light beam is separated into a plurality by multiplexing, thereby detecting different fluorescence intensities from a plurality of reaction containers.

According to Jpn. Pat. Appln. KOKAI Publication No. 09-113448, a plurality of reaction containers are arrayed in a line shape, one laser beam is applied to pass through all the reaction containers, a condenser lens is arranged in a front part in each reaction container to generate one focus in each of all the containers, and fluorescent correlation analysis is simultaneously carried out for samples in the reaction containers.

According to Jpn. Pat. KOKAI Publication No. 10-206742, at a laser scanning type confocal optical microscope, observation images of different times are obtained by two independent scanning optical systems, and dynamic characteristics of a sample are obtained based on a position movement when the images are superimposed together.

According to conventionally executed fluorescent correlation spectroscopy, a fluctuation of fluorescence intensity is observed from fluorescent molecules present in a visual field, and a time-sequential signal is accordingly obtained to calculate an auto-correlation function. In this case, if the fluorescent molecules present in the visual field are only one type, by directly analyzing the obtained fluctuation in fluorescence intensity, it is possible to obtain information regarding a translational diffusion speed or the like of the fluorescent molecules. Moreover, even if the fluorescent molecules move or change a motion speed, it is possible to statistically obtain such changes. If there are two or more types of fluorescent molecules different from each other in emission wavelength in a sample, by executing wavelength separation, it is possible to obtain an auto-correlation or a cross-correlation of the fluorescent molecules. However, such is limited in the same visual field.

In the case of observing an actual biological cell, real-time observation of behaviors of desired molecules inside/outside the cell or inside/outside a cell nucleus, and obtaining of changes with time or local information regarding phenomena such as signal transmission in the cell, material transportation and cell division are necessary. According to the conventional fluorescent correlation spectroscopy, a state change or behaviors of a group of molecules can be understood. However, it is impossible to dynamically measure a state change of a desired portion inside/outside the cell.

It is an object of the present invention to provide a biomolecule analyzer which can obtain various movements and changes of a target sample.

BRIEF SUMMARY OF THE INVENTION

A biomolecule analyzer of the present invention analyzes dynamic behaviors of biomolecules, and comprises image obtaining means for obtaining an image corresponding to at least one observation area of a biological sample containing biomolecules held in a measurable state; designation means for designating an arbitrary point on the image obtained by the image obtaining means; arrangement means for arranging a measuring point in a point position on the sample corresponding to the point designated by the designation means so that the measuring point may continuously coincide with the point position; measurement means for measuring a signal derived from dynamic information of an object to be measured from the measuring point arranged by the arrangement means; and analysis means for analyzing measuring results of the measurement means.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a view showing a configuration of a biomolecule analyzer according to a second embodiment of the present invention;

DETAILED DESCRIPTION OF THE INVENTION

Next, the embodiments of the present invention will be described with reference to the accompanying drawings.

Figure 1:
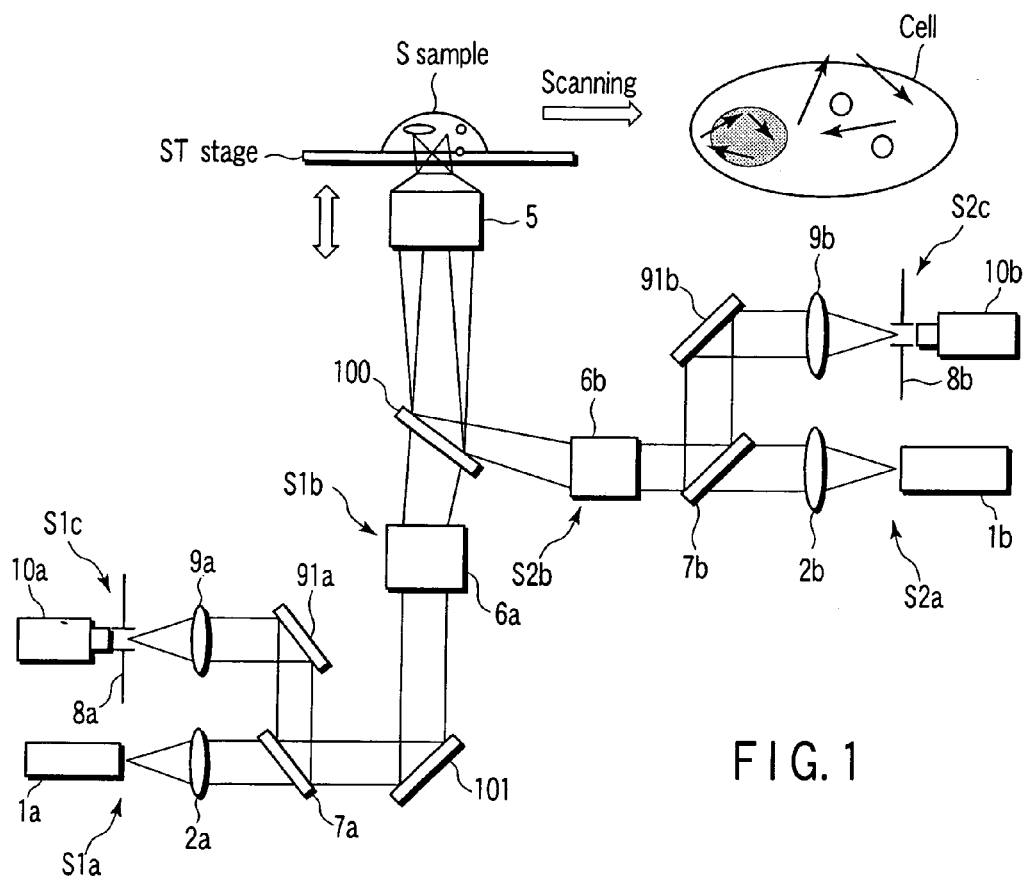
FIG. 1 is a view showing a basic configuration of a biomolecule analyzer according to a first embodiment of the present invention.

FIG. 1 is a view showing a basic configuration of a biomolecule analyzer according to a first embodiment of the invention. The invention uses a conventionally used laser scanning type confocal optical microscope as a base. According to the first embodiment, a very small measuring area is realized by a laser confocal optical system. To form a very small confocal area, an objective lens of a numerical aperture (NA) of about 1.0 is used. The confocal area thus obtained becomes roughly cylindrical in which a diameter is about 0.6 $\mu$m and a length is about 2 $\mu$m.

In FIG. 1, two illumination systems S1$a$, S2$a$, two scanning systems S1$b$, S2$b$, and two detection systems S1$c$, S2$c$ are disposed. The illumination systems S1$a$, S2$a$ respectively comprise laser beam sources 1$a$, 1$b$, and first lenses 2$a$, 2$b$. The scanning systems S1$b$, S2$b$ respectively comprise servo system galvanoscanners (galvanometer mirrors) 6$a$, 6$b$. The galvanoscanners 6$a$, 6$b$ are arranged so that scanning directions thereof can be in vertical directions, and each comprises an X-axis scanner and a Y-axis scanner which scan laser beams in X and Y axes. The detection systems S1$c$, S2$c$ respectively comprise light receiving lenses 9$a$, 9$b$, light receiving pinholes 8$a$, 8$b$, and photodetectors 10$a$, 10$b$.

First, to obtain an image of a biological sample (cell) S held in a measurable state on a stage ST, the first illumination system S1$a$, the first scanning system S1$b$ and the first detection system S1$c$ are used. A laser beam emitted from the laser beam source 1$a$ is passed through the first lens 2$a$, a dichroic mirror 7$a$, and a mirror 101 to reach the galvanoscanner 6$a$. The laser beam is subjected to XY scanning by the galvanoscanner 6$a$, and transmitted through a dichroic mirror 100 to illuminate the sample S on the stage ST through an objective lens 5.

A reflected light and fluorescence from the sample S is passed through the objective lens 5 and the dichroic mirror 100, and received by the 2-5 photodetector 10$a$ through the galvanoscanner 6$a$, the mirror 101, the dichroic mirror 7$a$, a mirror 91$a$, the receiving lens 9$a$, and the light receiving pinhole 8$a$. The photodetector 10$a$ measures a signal intensity. The optical signal is subjected to image processing such as contrast improvement or contour emphasis at an image processing device, and then guided to a computer to become a two-dimensional image on a TV monitor.

Next, to obtain an auto-correlation function of fluorescent molecules in the sample S, the second illumination system S2$a$, the second scanning system S2$b$, and the second detection system S2$c$ are used. A laser beam emitted from the laser beam source 1$b$ is passed through the first lens 2$b$ and the dichroic mirror 7$b$ to reach the galvanoscanner 6$b$. The laser beam is subjected to XY scanning by the galvanoscanner 6$b$, reflected by the dichroic mirror 100, and passed through the objective lens 5 to illuminate the sample S on the stage ST. Thus, the laser beam excites the fluorescent molecules in the sample S present in the very small measuring area, and a fluorescent signal (photon pulse) is obtained.

A fluctuation in intensity of the obtained fluorescent signal, i.e., fluorescence from the fluorescent molecules is passed through the objective lens 5 to be reflected by the dichroic mirror 100, and passed through the galvanoscanner 6$b$, the dichroic mirror 7$b$, the mirror 91$b$, the light receiving lens 9$b$, and the light receiving pinhole 8$b$ to be detected by the photodetector 10$b$. The fluorescent signal is converted into a photoelectric current pulse by the photodetector 10$b$, guided to a signal processing device to be subjected to waveform shaping, binarization or the like, and an auto-correlation function, a cross-correlation function or the like is obtained based on fluorescent correlation spectroscopy (FCS) by a computer (correlation analyzer). From the auto-correlation function obtained here, statistical properties such as a speed of translational diffusion motion of the fluorescent molecules are obtained. Incidentally, to subject the laser beam to XY scanning, not only the galvanoscanner but also an AO modulator (AOD) or a polygon mirror may be used.

Figure 2:
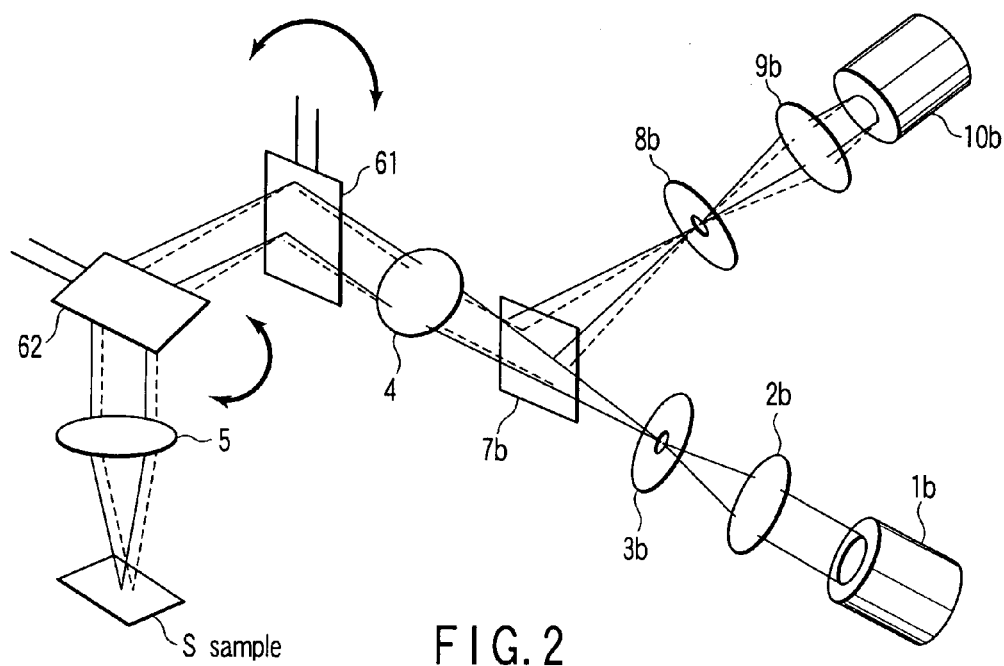
FIG. 2 is a view showing a basic configuration of a scanning optical system of the biomolecule analyzer according to the first embodiment of the invention.

FIG. 2 is a view showing basic configurations of the illumination optical system, the scanning optical system and the detection optical system of the biomolecule analyzer shown in FIG. 1. In FIG. 2, portions similar to those of FIG. 1 are denoted by similar reference numerals.

The laser beam emitted from the laser beam source 1b is focused by the first lens 2b. In a focusing position, an illumination light pinhole 3b is arranged. A position of the illumination light pinhole 3b is aligned with a focusing position of the second lens 4. The second lens 4 guides a collimated light (parallel light) to the objective lens 5. Additionally, a sample surface is aligned with a focusing position of the objective lens 5.

The laser beam emitted from the laser beam source 1b is passed through the first lens 2b and the illumination light pinhole 3b and through, the dichroic mirror 7b, and passed through the second lens 4 to reach an X-axis scanner 61 and a Y-axis scanner 62. Scanning directions of the X-axis scanner 61 and the Y-axis scanner 62 are orthogonal to each other. The laser beam is subjected to X-axis scanning and Y-axis scanning by the X-axis scanner 61 and the Y-axis scanner 62, and two-dimensionally scanned in the sample S surface.

The fluorescent signal from the fluorescent molecules in the sample S is passed through the same optical path as that of the emitted laser beam to be reflected by the dichroic mirror 7b arranged between the second lens 4 and the illumination light pinhole 3b. This reflected light is passed through the light receiving pinhole 8b arranged in a focusing position of the second lens 4 to be guided to the light receiving lens 9b. The dichroic mirror 7b has spectral characteristics that pass the emitted laser beam (exciting light) and reflect the fluorescent emitted from the fluorescent molecules. The light receiving pinhole 8b is set in a focusing position of the light receiving lens 9b. The fluorescence is passed through the light receiving lens 9b to reach the photodetector (light receiver) 10b. For the photodetector 10b, a two-dimensional photodetector such as a CCD camera for obtaining images is used. To measure a fluctuation of fluorescent intensity, an avalanche photodiode (APD), a photoelectron multiplier or the like is used.

Figure 3:
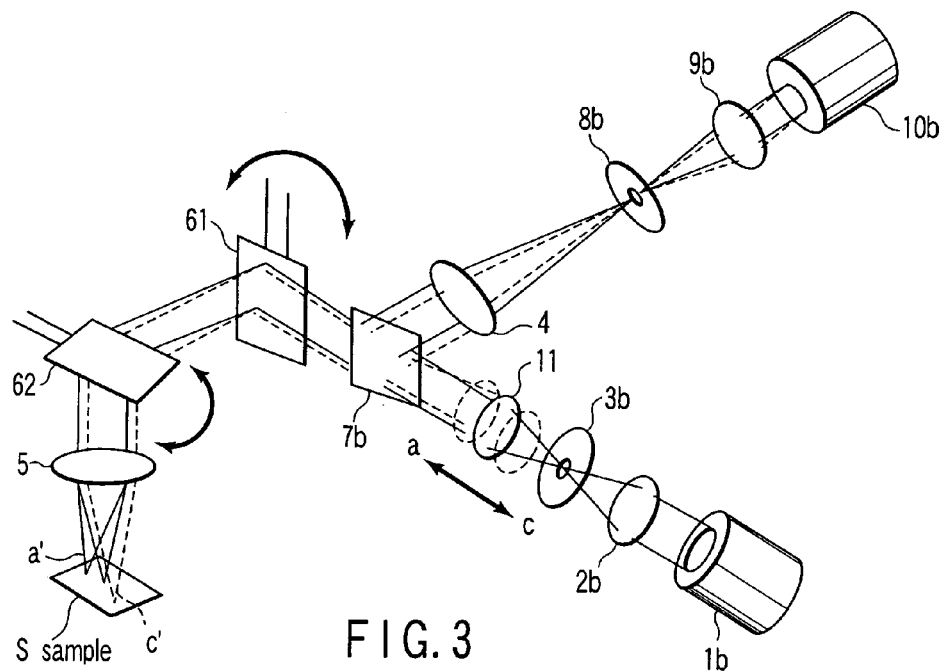
FIG. 3 is a view showing a specific configuration of the scanning optical system of the biomolecule analyzer according to the first embodiment of the invention.

FIG. 3 is a view showing a specific configuration of the scanning optical system of the biomolecule analyzer shown in FIG. 1. In FIG. 3, portions similar to those of FIG. 2 are denoted by similar reference numerals. Hereinafter, three-dimensional scanning of a laser beam will be described by referring to FIG. 3.

The optical system of FIG. 3 is constructed to implement a focusing movement in an optical axis direction (Z-axis direction). In FIG. 3, a movable lens 11 is arranged between the illumination light pinhole 3b and the dichroic mirror 7b shown in FIG. 2. By moving the movable lens 11 by a proper amount in the optical axis direction, a focusing position of the laser beam source 1b on the sample surface can be changed in the optical axis direction (Z-axis direction). For example, when the movable lens 11 is moved in a direction of a, the focusing position on the sample surface becomes a'. Conversely, when the movable lens is moved in a direction of c, the focusing position on the sample surface becomes c'.

By moving the movable lens 11 in such a manner, a light flux passed therethrough is provided with a spreading angle corresponding to a moving amount thereof. Thus, the focusing position of the emitted laser beam passed through the objective lens 5 can be moved by a proper amount in the optical axis direction. Further, three-dimensional scanning can be carried out, a focus of the emitted laser beam is aligned with a sample depth direction with respect to a three-dimensional position in the sample, whereby desired fluorescent molecules distributed in the depth direction can be excited.

Incidentally, the focusing movement in the optical axis direction (Z-axis direction) can be implemented by moving the objective lens 5 in the optical axis direction.

Figure 4:
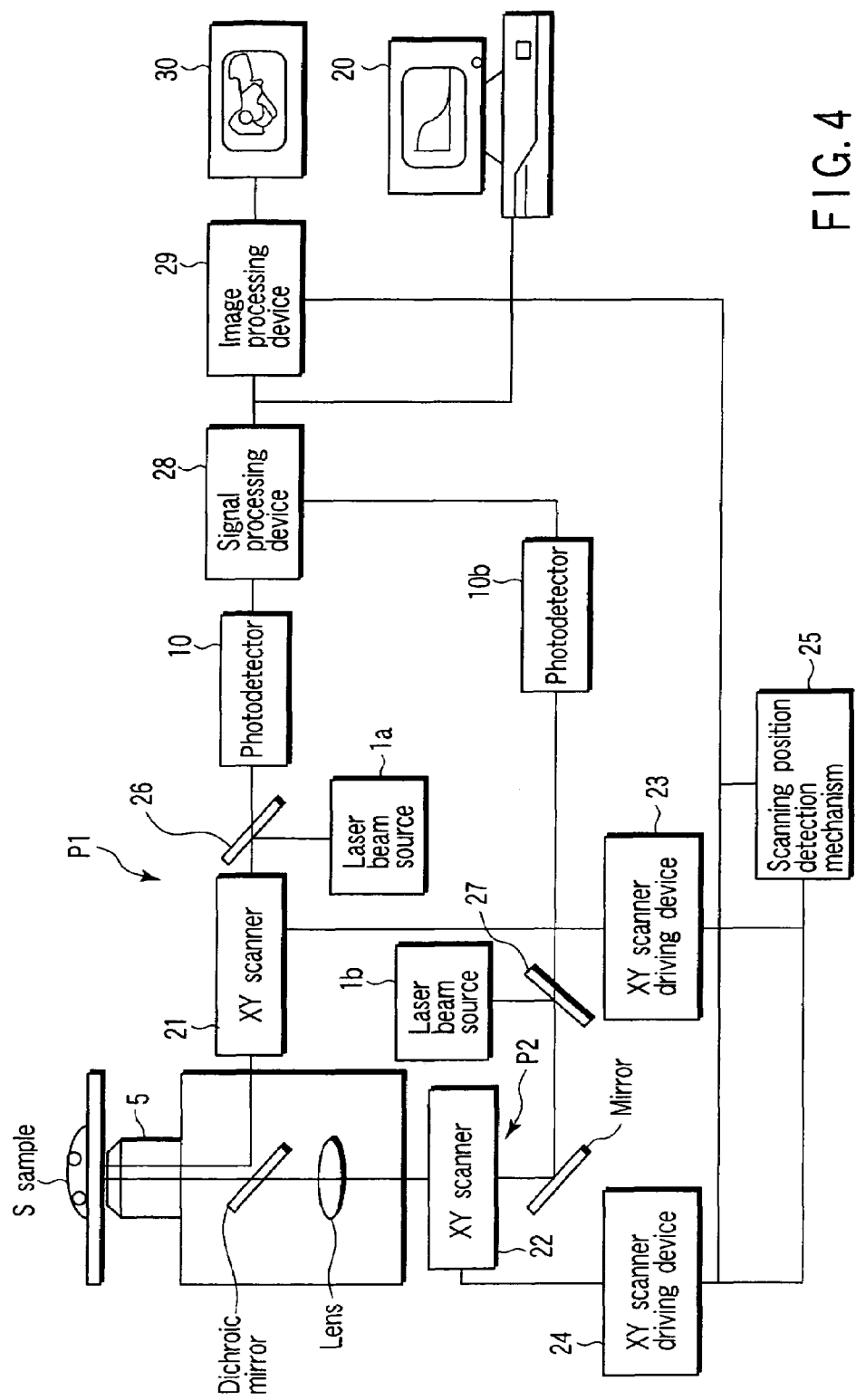
FIG. 4 is a view showing a specific configuration of the biomolecule analyzer according to the first embodiment of the invention.

FIG. 4 is a view showing a specific configuration of the biomolecule analyzer according to the first embodiment of the invention. Hereinafter, an operation of the biomolecule analyzer will be described by referring to FIG. 4. By this analyzer, a two-dimensional or three-dimensional image is obtained on the TV monitor by the laser scanning type confocal optical microscope. As an XY scanner 21 to obtain a two-dimensional image, XY scanning is carried out by using, e.g., a galvanoscanner. For example, this is set as a first scanning system P1. As another XY scanner 22, the same galvanoscanner as that of the first scanning system P1 is used and, for example, this is set as a second scanning system P2.

In the case of obtaining an observed image by a microscope, for example, by XY scanning of the first scanning system P1, a laser beam is applied into a cell, a reflected light and fluorescence are detected by the photodetector 10a, a light intensity signal is converted into an electric signal, and a waveform is shaped by a signal processing device 28. Then, a two-dimensional image is generated by an image processing device 29, and output to a TV monitor 30. Additionally, by moving the movable lens or the objective lens 5 in the optical axis direction, a focusing position of the laser beam can be moved up and down in the optical axis direction. Thus, a three-dimensional image can be generated on the TV motor 30.

The two XY scanners 21, 22 are arranged to execute scanning separately each other, and scanning motion thereof is accurately controlled by XY scanner driving devices 23, 24 controlled by a computer 20. A scanning position detection mechanism 25 is disposed for the XY scanner driving devices 23, 24 to accurately detect a scanning position in real time, and the scanning position is fed back to the computer 20 to be controlled. Accordingly, by random scanning in the sample S, it is possible to simultaneously measure two fluorescent signals from fluorescent molecules present in desired positions in the sample S. Incidentally, by causing the computer 20 to control the XY scanner driving devices 23, 24, it is possible to obtain a plurality of fluorescent signals different in time from the same position in the sample S.

For a laser as an exciting light, an argon laser of a wavelength 488 nm, or an He.Ne laser of a wave-length 633 nm is used. For a fluorescent dye that indicates a desired place in the cell of the sample S, rhodamine green (RhG), or cyfive (Cy5) is used. The rhodamine green (RhG) is excited by the argon laser of a wavelength 488 nm from the laser beam source 1a. The cyfive (Cy5) is excited by the He.Ne laser of a wavelength 633 nm from the laser beam source 1b. Fluorescence from fluorescent dye molecules of desired places is passed through the same path as that of an exciting light, separated from an incident optical path by dichroic mirrors 26, 27 optically adjusted according to emission wavelengths of dyes, and detected by the photodetectors 10a, 10b.

A light intensity signal that has entered the photodetectors 10a, 10b is converted into an electric signal, a waveform is shaped by the signal processing device 28, converted into an on-off binary pulse, and guided to the computer 20. The computer 20 executes a correlation operation for the input binary pulse signal to obtain an auto-correlation function.

Further, from the obtained auto-correlation function, a change in a translational diffusion speed of the fluorescent molecules or the number of fluorescent molecules in the measuring area, or the like is obtained. If the light intensity signal which enters the photodetectors 10a, 10b is relatively large, an electric signal output from each of the photodetectors 10a, 10b becomes a time-sequential signal. In this case, the time-sequential signal is subjected to A/D conversion by the signal processing device 28 to be converted into a digital signal. Then, a waveform is shaped, and the digital signal is converted into a binary pulse signal as in the previous case. By guiding this binary pulse signal to the computer 20, a correlation operation is carried out to obtain an auto-correlation function. Alternatively, the digitized time-sequential signal may be directly guided to the computer 20, and a correlation operation may be executed.

Designation of a scanning point on the observed image is carried out as follows. An observer discovers a light emitted from a fluorescent molecule of a desired point while watching the observed image on the TV monitor 30. To stop scanning of the scanning mirror of the XY scanners 21, 22 at this point, the observer designates a point on the image by designation means accessory to the computer 20, e.g., a keyboard, a mouse pointer or the like, and transmits positional information to the scanning mirror driving mechanism 25, whereby an optical axis is adjusted. Accordingly, a measuring point is arranged in a three-dimensional optional position of the sample S. An angle of the scanning mirror in this case is accurately obtained by the scanning position detection mechanism 25.

Figure 5:
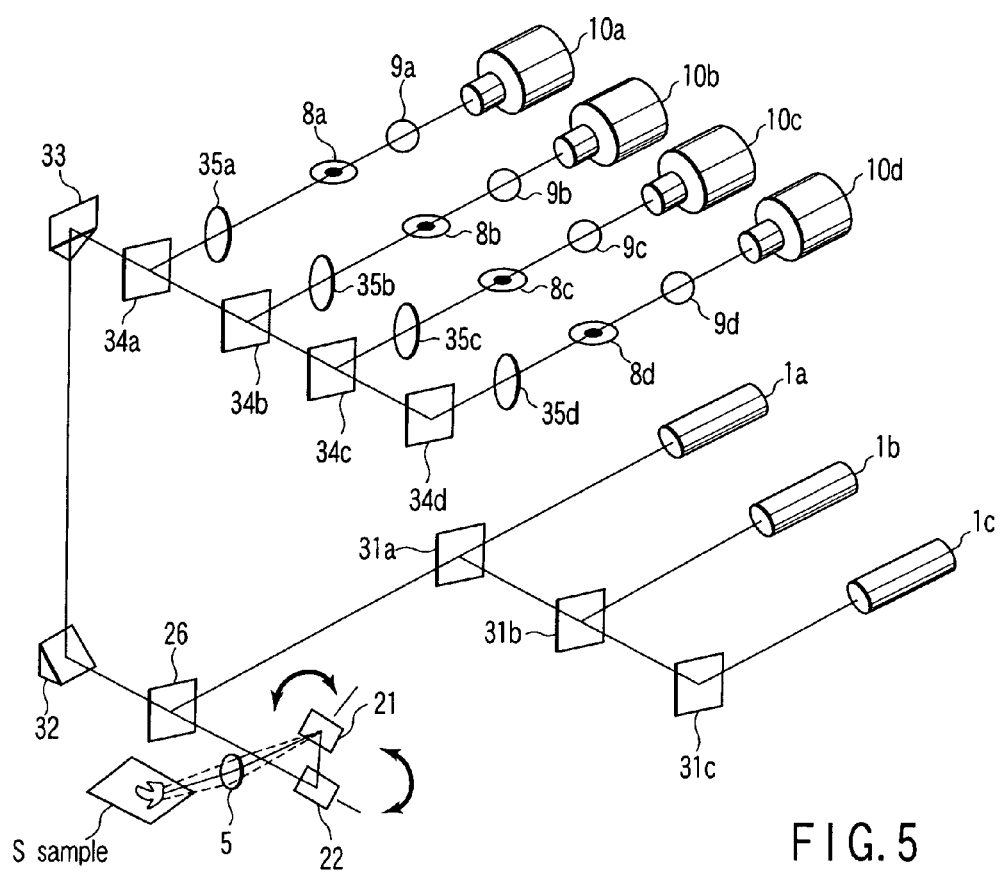
FIG. 5 is a view showing a configuration of the scanning optical system which uses a number of laser beam sources and a number of photodetectors according to the first embodiment of the invention.

FIG. 5 is a view showing a configuration in which a number of illumination optical systems and a number of detection optical systems are used. Hereinafter, measurement that uses a number of laser beam sources and a number of photodetectors will be described by referring to FIG. 5. The configuration of FIG. 5 is basically similar to that of one scanning optical system, one detection optical system. As shown in FIG. 5, three laser beam sources 1a, 1b, and 1c, and four photodetectors 10a, 10b, 10c and 10d are disposed.

The laser beam source 1a comprises an argon laser of a wavelength 488 nm, the laser beam source 1b comprises an argon laser of a wavelength 514.5 nm, and the laser beam source 1c comprises a helium neon laser of a wavelength 632.8 nm. For fluorescent dyes in a sample S, rhodamine green (RhG), tetramethyl rhodamine (TMR), and cyfive (Cy5) are used. The rhodamine green (RhG) is excited by the argon laser of a wavelength 488 nm. The tetramethyl rhodamine (TMR) is excited by the argon laser of a wavelength 514.5 nm. The cyfive (Cy5) is excited by the helium neon laser of a wavelength 632.8 nm. Each fluorescent dye indicates a desired target molecule in a cell, e.g., a base or cholesterol constituting DNA. Thus, information regarding a structural change such as aggregation of the cholesterol taken into the cell is obtained.

A laser beam emitted from the laser beam source 1a is passed through a dichroic mirror 31a, and reflected by a dichroic mirror 26 to reach an XY scanner 21 and an XY scanner 22. A lased beam emitted from the laser beam source 1b is reflected by a dichroic mirror 31b, reflected by a dichroic mirror 31a, and reflected by the dichroic mirror 26 to reach the XY scanner 22 and the XY scanner 21. A laser beam emitted from the laser beam source 1c is reflected by the dichroic mirror 31c, passed through the dichroic mirror 31b, reflected by the dichroic mirror 31a, and reflected by the dichroic mirror 26 to reach the XY scanner 21 and the XY scanner 22. The laser beam is scanned in the sample S surface through an objective lens 5 by the XY scanner 21 and the XY scanner 22.

A reflected light and fluorescence from the sample S are passed through the objective lens 5, the XY scanner 21 and the XY scanner 22, and through the dichroic mirror 26, reflected by a mirror 32, and reflected by a mirror 33. The reflected light and the fluorescence reflected by the mirror 33 and reflected by the dichroic mirror 34a are passed through a lens 35a, a light receiving pinhole 8a and a light receiving lens 9a, and detected by a photodetector 10a. Similarly, the reflected light and the fluorescence passed through the dichroic mirror 34a and reflected by the dichroic mirrors 34b, 34c and 34d are passed through lenses 35b, 35c and 35d, light receiving pinholes 8b, 8c and 8d, and light receiving lenses 9b, 9c and 9d, and detected by photodetectors 10b, 10c and 10d.

In FIG. 5, one of the laser beam sources is shared as a scanning optical system, an observation optical system. One laser beam source may be added to make the number of sources 4, one of them may be used as an observation optical system to obtain a sample image, while the other three may be used for fluorescent excitation. Additionally, the number of laser beam sources is not limited to 4, but it may be 5 or more.

Thus, by using the two XY scanners 21, 22, scanning operations are carried out in directions orthogonal to each other. The first embodiment employs the configuration in which the two XY scanners are shared by the laser beam sources 1a, 1b and 1c, and the laser beams are scanned in the same direction. However, the invention is not limited to such. By using 4 or 6 XY scanners, laser beams may be scanned in different directions.

Additionally, an angle of the XY scanner is detected by the scanning position detection mechanism, the XY scanner is fixed in the position, a laser beam is applied to a target molecule position of the sample, and a fluorescent signal is detected from the target molecule. Fluorescent signals emitted from the fluorescent molecules are detected by the different photodetectors 10a, 10b, 10c, and 10d. Obtained time-sequential pulse signals are subjected to waveform shaping, binarization at the signal processing device, guided to the computer, and subjected to correlation operations to obtain auto-correlation functions.

According to the first embodiment, it is possible to simultaneously capture behaviors of target molecules such as different proteins in the same cell in real time. Moreover, it is possible to obtain information for correlations of different target molecules.

FIG. 6 is a view showing a configuration of a biomolecule analyzer according to a second embodiment of the present invention. In FIG. 6, portions similar to those of FIG. 1 are denoted by similar reference numerals.

In FIG. 6, four illumination systems S11a, S12a, S22a and S32a, three scanning systems S11b, S12b and S13b, and four detection systems S11c, S12c, S22c and S32c are disposed. The illumination systems S11a, S12a, S22a and S32a respectively comprise laser beam sources 11a, 11b, 21b and 31b, and first lenses 12a, 12b, 22b and 32b. The scanning systems S11b, S12b and S13b respectively comprise servo system galvanoscanners (galvanometer mirrors) 16a, 16b and 16c. Each of the galvanoscanners 16a, 16b and 16c comprises an X-axis scanner and a Y-axis scanner. The detection systems S11c, S12c, S22c and S32c respectively comprise light receiving lenses 19a, 19b, 29b and 39b, light receiving pinholes 18a, 18b, 28b and 38b, and photodetectors 110a, 110b, 210b and 310b.

First, to obtain an image of a biological sample (cell) S held in a measurable state on a stage ST, the first illumination system S11a, the first scanning system S11b and the first detection system S11c are used. A laser beam emitted from the laser beam source 11a is passed through the first lens 12a and a dichroic mirror 17a to reach the galvanoscanner 16a. The laser beam is subjected to XY scanning by the galvanoscanner 16a, reflected by a dichroic mirror 102, and transmitted through a dichroic mirror 103 to illuminate the sample S on the stage ST through an objective lens 5.

A reflected light and fluorescence from the sample S are passed through the objective lens 5 and the dichroic mirror 103, reflected by the dichroic mirror 102, and detected by the photodetector 110a through the galvanoscanner 16b, the dichroic mirror 17a, a mirror 191a, the receiving lens 19a, and the light receiving pinhole 18a. The photodetector 110a measures intensity of an optical signal. The optical signal is subjected to image processing such as contrast improvement or contour emphasis at an image processing device, and then guided to a computer to become a two-dimensional image on a TV monitor.

Next, to obtain an auto-correlation function of fluorescent molecules in the sample S, for example, the second illumination system S12a, the second scanning system S12b, and the second detection system S12c are used. A laser beam emitted from the laser beam source 11b is passed through the first lens 12b, the dichroic mirror 17b and a mirror 104 to reach the galvanoscanner 16b. The laser beam is subjected to XY scanning by the galvanoscanner 16b, reflected by the dichroic mirror 103, and passed through the objective lens 5 to illuminate the sample S on the stage ST. Thus, as in the case of the first embodiment, the laser beam excites the fluorescent molecules in the sample S present in a very small measuring area, and a fluorescent signal (photon pulse) is obtained.

A fluctuation in intensity of the obtained fluorescent signal, i.e., fluorescence from the fluorescent molecules, is passed through the objective lens 5 to be reflected by the dichroic mirror 103, and passed through the galvanoscanner 16b, the mirror 104, the dichroic mirror 17b, the mirror 191b, the light receiving lens 19b, and the light receiving pinhole 18b to be detected by the photodetector 110b. The fluorescent signal is converted into a photoelectric current pulse by the photodetector 110b, guided to a signal processing device to be subjected to waveform shaping, binarization or the like, and an auto-correlation function, a cross-correlation function or the like is obtained based on fluorescent correlation spectroscopy (FCS) by a computer (correlation analyzer). From the auto-correlation function obtained here, statistical properties such as a speed of translational diffusion motion of the fluorescent molecules are obtained.

In the aforementioned example, to obtain the correlation function of the fluorescent molecules, the combination of the second illumination system S12a, the second scanning system S12b and the second detection system S12c is used. However, other combinations, such as a combination of the third illumination system S22a, the second scanning system S12b, and the third detection system S22c, and a combination of the fourth illumination system S32a, the third scanning system S13b, and the fourth detection system S32c can be used. That is, by the optical systems, auto-correlation functions or cross-correlation functions can individually be obtained from fluorescent molecules present in desired different portions of the sample. The galvanoscanners 16a, 16b and 16c operate independently of one another to converge laser beam spots on a plurality of different portions of the sample. Alternatively, the galvanoscanners 16a, 16b and 16c may be cooperatively operated to simultaneously converge laser beam spots on one desired portion of the sample.

According to the second embodiment, the number of types of fluorescent dyes is one. For example, rhodamine green (RhG) is used, and an argon laser (wavelength 488 nm) is used for a laser. An output light intensity of the argon laser is set to, e.g., 10 mW. As the output light intensity of the laser is larger, a fluorescent dye can be excited more strongly, and stronger fluorescence can be received. However, if the output light intensity of the laser is too large, background noise may be increased, and the fluorescent dye may be faded. Thus, the output light intensity of about 10 mW is proper though dependent on a device configuration.

According to the second embodiment, a fluctuation in fluorescent intensity from the fluorescent molecules present in the desired different portions of the sample is detected by the photodetector, and guided to the correlation analyzer. Thus, it is possible to know a state or a size of the cell to which the fluorescent dye has been added from the obtained auto-correlation function or cross-correlation function.

Figure 7:
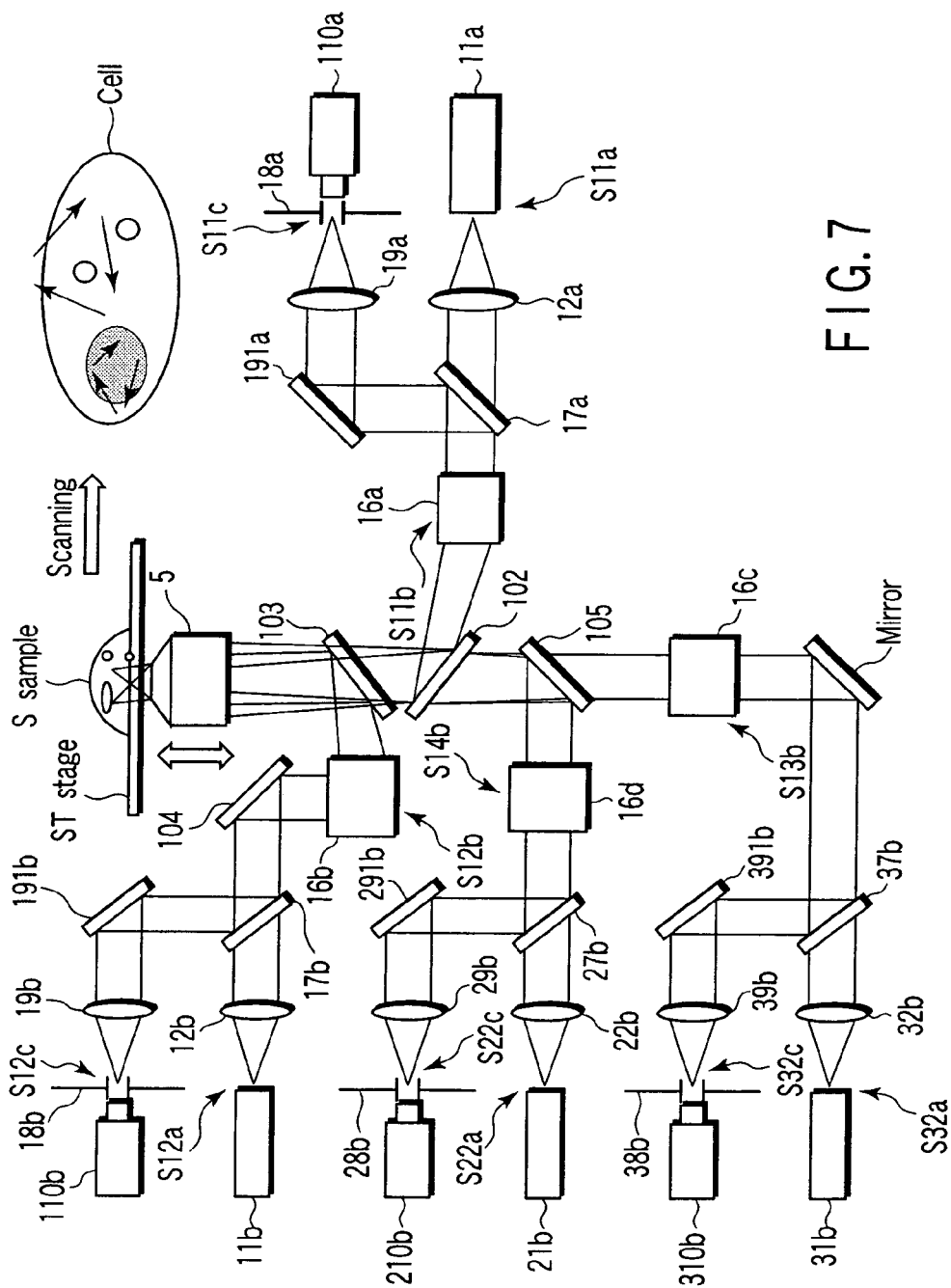
FIG. 7 is a view showing a configuration of a biomolecule analyzer according to a third embodiment of the present invention.

FIG. 7 is a view showing a configuration of a biomolecule analyzer according to a third embodiment of the present invention. In FIG. 7, portions similar to those of FIG. 6 are denoted by similar reference numerals.

In FIG. 7, four scanning systems S11b, S12b, S13b and S14b are disposed. An operation process of obtaining an image of a biological sample (cell) S held in a measurable state on a stage ST is similar to that of the second embodiment. Additionally, an operation process when a second illumination system S12a, a second scanning system S12b and a second detection system S12c are used to obtain an auto-correlation function of fluorescent molecules in the sample S is similar to that of the second embodiment.

To obtain an auto-correlation function of fluorescent molecules in the sample S, for example, a third illumination system S22a, the fourth scanning system S14b, and a third detection system S22c are used. A laser beam emitted from a laser beam source 21b is passed through a first lens 22b and a dichroic mirror 27b to reach a galvanoscanner 16d. The laser beam is subjected to XY scanning by the galvanoscanner 16d, reflected by a dichroic mirror 105, and passed through a dichroic mirror 102, a dichroic mirror 103 and an objective lens 5 to illuminate the sample S on the stage ST. Thus, as in the case of the first and second embodiments, the laser beam excites the fluorescent molecules in the sample S present in a very small measuring area, and a fluorescent signal (photon pulse) is obtained.

A fluctuation in intensity of the obtained fluorescent signal, i.e., fluorescence from the fluorescent molecules, is passed through the objective lens 5, the dichroic mirror 103 and the dichroic mirror 102 to be reflected by the dichroic mirror 105, and passed through the galvanoscanner 16d, a dichroic mirror 27b, a mirror 291b, a light receiving lens 29b, and a light receiving pinhole 28b to be detected by a photodetector 210b. Additionally, in the case of using a fourth illumination system S32a, the third scanning system S13b and a fourth detection system S32c, the laser beam is subjected to XY scanning by a galvanoscanner 16c.

According to the third embodiment, a set of galvanoscanners is used for each optical system which comprises a combination of the laser beam source, the first lens, the dichroic mirror, the mirror, the light receiving lens, the light receiving pinhole, and the photodetector. Among such optical systems, laser oscillation wavelengths are different, and wavelength characteristics of the dichroic mirrors are different.

By such a configuration, laser beams of different wavelengths can be simultaneously converged substantially on the same converging position by the optical systems, and fluorescence from each of different fluorescent dyes can be detected. Additionally, by the optical systems, the laser beams can be applied to different portions of the sample through the same objective lens. Thus, since scanning operations are executed by the independently operated galvanoscanners at the optical systems, the laser beams are applied to different positions by the optical systems. As a result, laser beam spots can be converged on a plurality of discrete portions of the sample simultaneously or by shifted timings.

For one optical system that comprises a combination of a laser beam source, a first lens, a dichroic mirror, a mirror, a light receiving lens, a light receiving pinhole and a photodetector, two or more sets of scanning systems that comprise galvanoscanners may be used.

According to the third embodiment, laser beams of a single or a plurality of different wavelengths, or a plurality of laser beams of a plurality of different wavelengths are applied to desired different portions of the sample simultaneously or at different timing to obtain fluorescence from the fluorescent molecules, the fluorescence is recorded and observed as an image, and an auto-correlation function or a cross-correlation function can be obtained from a fluctuation in fluorescent intensity by an operation.

Hereinafter, description will be made of a method of correcting dynamic and static characteristics in the biomolecule analyzer of each of the first to third embodiments.

In the case of selecting an optional point displayed in an image obtained by the laser microscope, and executing fluorescent analysis for one molecule by fluorescent correlation spectroscopy (FCS), the image obtained by the laser microscope is drawn by driving the scanning means at a high speed. Thus, even when the scanning means receives the same control signal to be made static, it generally stops at a different position. Especially, an influence thereof is conspicuous in mechanical scanning means such as a galvanoscanner. Therefore, to correctly stop a laser beam with respect to a target displayed in the image obtained by the laser microscope, certain correction means is necessary.

1) Method Using Standard Chart

Figure 8A:
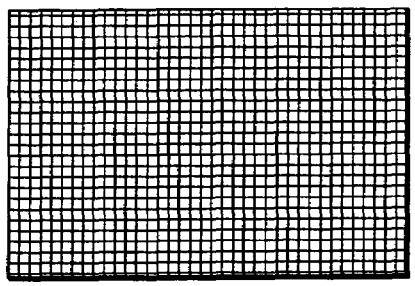
FIGS. 8A and 8B are views each of which shows an example of a standard chart according to a fourth embodiment of the present invention.
Figure 8B:
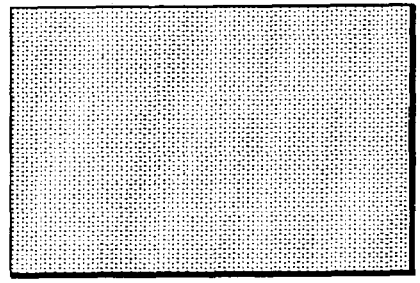

FIGS. 8A and 8B are views showing examples of standard charts: FIG. 8A showing a lattice pattern, and FIG. 8B showing a random pattern. According to this method, a standard chart is prepared, and scanning is executed at a low speed to make dynamic characteristics similar to static characteristics, thereby obtaining image data. The image data is compared with image data obtained by normal high-speed scanning to obtain correction data.

Components to realize the method are a first memory for recording the image obtained by the normal high-speed scanning, a second memory for recording the image obtained by the low-speed scanning, an arithmetic unit for comparing the two images recorded in the first memory and the second memory with each other, a third memory for recording comparison results (correction data) of the arithmetic unit, and a correction device for converting a position designated on the image obtained by the laser microscope into control data by using the correction data. Incidentally, the memory, the arithmetic unit and the correction device are normally realized by computers.

Hereinafter, a process of a method that uses a standard chart will be described. Standard image data constituting the standard chart may be lattice data, random data and the like shown in FIGS. 8A and 8B.

First, an image is obtained by normal high-speed scanning, and recorded in the first memory. Then, an image is obtained by low-speed scanning, and recorded in a second memory. Next, at the arithmetic unit, the image obtained by the high-speed scanning and the image obtained by the low-speed scanning are compared with each other for positional shifting or distortion, and results of the comparison are recorded in the third memory. For this comparison, a correlation operation is normally used. Next, at the arithmetic unit, correction data of a control signal of the image obtained by the low-speed scanning is created with respect to a control signal of the image obtained by the high-speed scanning. Usually, this correction data is a voltage value for controlling a scanning angle. Incidentally, the correction data is created for each high scanning speed, each scanning angle.

Figure 9:
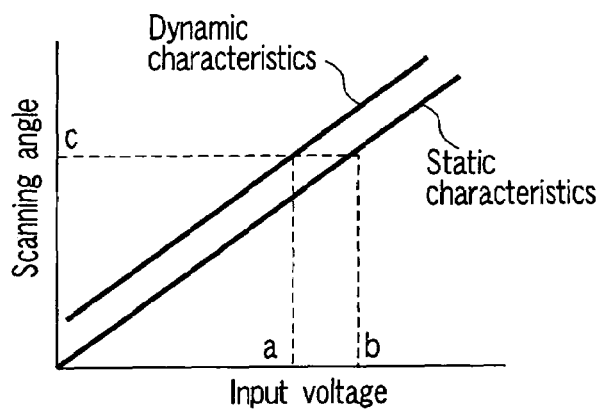
FIG. 9 is a view showing dynamic and static characteristics of a scanning angle with respect to an input voltage according to the fourth embodiment of the invention.

FIG. 9 is a view showing dynamic characteristics and static characteristics of a scanning angle with respect to an input voltage. Hereinafter, referring to FIG. 9, the method will be described more specifically. In the middle of high-speed scanning by the laser microscope, it is difficult to specify a place (position on image) of a scanning angle with respect to a voltage level. In reality, a coordinate on an image is decided based on a voltage as an axis.

Thus, first, as shown in FIG. 9, an observation point c is selected from the image obtained by the low-speed scanning to obtain a voltage b. Next, an observation point c (voltage a) is discovered in the image obtained by the high-speed scanning, and a difference in position from the image obtained by the low-speed scanning is obtained. This difference is a difference between static characteristics and dynamic characteristics. By setting the correction data in the entire region of the image using the standard chart, correction can be made in an optional position.

In the case of actually designating an observation point in the image, an observation point is designated on the image obtained by the high-speed scanning. In the case of stopping a laser beam on the observation point, a voltage b is input by using the correction data. Accordingly, the laser beam can be correctly fixed in an optional position designated on the image obtained by the laser microscope to enable FCS measurement. By this method, all errors of the optical system such as distortion can be corrected.

2) Method Using Fluorescent Sample

The scanning means is stopped to apply a laser beam to a sample on which a fluorescence dye has been uniformly coated, thereby fading it. For a fading method, a lattice point or other patterns may be used. Next, a fluorescent image obtained by normal high-speed scanning and the laser microscope is observed. Then, a faded pattern appears on the image. From image shifting at this time, a difference between dynamic characteristics and static characteristics becomes apparent.

Figure 10:
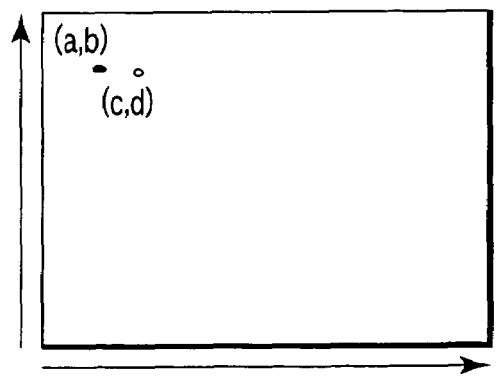
FIG. 10 is a view showing an image recorded in an image memory according to the fourth embodiment of the invention.

FIG. 10 is a view showing an image recorded in the image memory. Each pixel of the image can be considered to have been recorded based on an angle of the scanning means or a control voltage (control input) as an axis at the time of sampling. First, the scanning means is stopped to fade the fluorescent dye. A control input to the scanning means at this time is set to (a, b). Next, a fluorescent image obtained by the normal laser microscope is observed, and a coordinate of checked fading is set to (c, d). A difference between the (a, b) and the (c, d) is a difference between static characteristics and dynamic characteristics.

As one of the methods of obtaining the difference, a correlation operation is generally available. By carrying out such work over the entire surface of the image at certain intervals, correction data can be obtained. Meticulous correction for each pixel can be implemented by interpolating correction data which has been obtained by experiment. For actual position designation, an observation position is designated (e.g., (c, d)) on the image obtained by the normal laser microscope, and converted into (a, b) by using the correction data, whereby accurate control can be executed. By the aforementioned method, it is possible to accurately set an observation point from a microscopic image.

According to the invention, as light sources for exciting fluorescent dye molecules, a plurality of continuous oscillation lasers or pulse lasers are selected (laser wavelengths are selected) and used according to measuring points, a plurality of desired points in the area in the cell are excited, and a fluctuation in fluorescence intensity is measured, whereby translational diffusion motion of a plurality of types of fluorescent molecules can be analyzed. According to the method, a plurality of target molecules inside/outside a cell or inside/outside a cellularity can be obtained as targets. Analysis can be carried out by observing and recording dynamic changes such as signal transmission in the cell, material transportation and cell division three-dimensionally in real time. Additionally, since transfer control reaction or an information transmission system inside/outside the cell nucleus can become apparent, it is possible to provide useful information in genome new drug research. These have not been realized by the conventional fluorescent correlation spectroscopy measurement.

In the case of measuring a cross-correlation for two types of desired molecules in the cell, a time-sequential signal of a fluorescent intensity fluctuation (signal derived from molecule dynamic information) is analyzed by indicating the molecules by different fluorescent dyes and simultaneously detecting fluorescent signals in parallel. Thus, a correlation of both becomes apparent, and information regarding the number of free molecules, the number of coupled molecules or the like can be obtained. Moreover, the method is suited to simultaneously measuring responsiveness to one or more stimulants with time in two or more discrete positions.

Even in the same cell, between a deep part near the nucleus and the vicinity of a cell membrane near the outside, various differences are conceivable such as a difference in PH, ion concentration gradient, oxygen concentration, and uneven distribution of proteins. Especially, in the nucleus, flowing in or out of proteins such as transfer factors, formation or dissociation of transfer composites, or the like occurs to cause dynamic changes from time to time. According to the invention, not only such changes of a plurality of discrete places in the cell are converted into images in real time but also behaviors thereof are statistically analyzed to unravel motion changes. Moreover, it is possible to obtain information regarding correlations.

As described above, according to the embodiment, by using the confocal scanning type optical microscope as a base, a laser beam is applied to a biological sample in which specific portions within a visual field are indicated by fluorescent dyes, a fluctuation in fluorescent intensity from a plurality of specific portions in the sample is subjected to correlation analysis while a sample image is observed and recorded, and statistical properties of the portions or an interaction therebetween is obtained.

That is, desired fluorescent molecules discretely present in the sample are recognized, a two-dimensional or three-dimensional image within the visual field is recognized and recorded, and fluctuations in fluorescence intensity from the fluorescent molecules are simultaneously or separately detected while positions on the sample image are detected.

Then, an auto-correlation function of the intensity fluctuation (serial signal) of each fluorescent molecule is analyzed, and a cross-correlation analysis between desired different fluorescent molecules is analyzed. Thus, a time and spatial relation between measuring points can be analyzed.

As described above, while a plurality of portions in the same cell are identified, observed and recorded, fluorescent signals from the portions are individually received to execute correlation analysis, and statistical properties (diffusion speed, particle concentration or the like of each portion, a correlation between different portions or the like is obtained. Thus, it is possible to obtain dynamic behaviors or changes in statistical properties from a plurality of desired portions present in the same cell which has conventionally been impossible to be analyzed.

Furthermore, since correlation analyses can be simultaneously executed at a plurality of portions, it is possible to analyze comparison and examination of the functions of the different components in the same cell in real time. Similarly, cells different in structure can be simultaneously compared. Further, changes with time in different portions in the cell or between the cells can be analyzed by simultaneous comparison and examination. Incidentally, in the case of investigating an abnormality such as a cancer for each living cell, a desired target portion can be highly accurately and quickly analyzed. Thus, reliability of cell diagnosis is improved, and a great contribution can be made to pathological or regeneration medicine.

According to the invention, the following biomolecule analyzer is configured.

(1) A biomolecule analyzer which analyzes dynamic behaviors of biomolecules, comprising: image obtaining means for obtaining an image corresponding to at least one observation area of a biological sample containing biomolecules held in a measurable state; designation means for designating an optional point on the image obtained by the image obtaining means; arrangement means for arranging a measuring point in a position on the sample corresponding to the point designated by the designation means; measurement means for measuring a signal derived from dynamic information of a material to be measured from the measuring point arranged by the arrangement means; and analysis means for analyzing measuring results of the measurement means.

(2) The biomolecule analyzer according to (1), wherein: the image obtained by the image obtaining means contains a three-dimensional area; and the arrangement means arranges the measuring point on an optional three-dimensional point.

(3) The biomolecule analyzer according to (1), wherein: the measurement means obtains a plurality of signals different in time from the same measuring point, and the analysis means compares outputs between the measuring points, and executes an operation.

(4) The biomolecule analyzer according to (1), wherein the measurement means measures an intensity of an optical signal.

(5) The biomolecule analyzer according to (1), wherein the analysis means measures a fluctuation in fluorescence intensity.

(6) The biomolecule analyzer according to claim (5), wherein the analysis means measures the fluctuation in fluorescence intensity based on fluorescent correlation spectroscopy.

(7) The biomolecule analyzer according to (1), wherein the image obtaining means comprises a laser scanning type confocal system.

(8) The biomolecule analyzer according to (5), wherein the image obtaining means scans the sample by using a galvanoscanner.

(9) The biomolecule analyzer according to (1), wherein the measurement means comprises a confocal optical system.

(10) The biomolecule analyzer according to (1), wherein the image obtaining means can select a wavelength according to a measuring point on the sample.

(11) The biomolecule analyzer according to (1), wherein the analysis means executes correlation analysis for the different materials to be measured based on an auto-correlation and a cross-correlation.

(12) The biomolecule analyzer according to (11), wherein a scanning optical system used for the correlation analysis is similar to that of the image obtaining means.

(13) The biomolecule analyzer according to (11), wherein a scanning optical system used for the correlation analysis is different from that of the image obtaining means.

(14) The biomolecule analyzer according to (11), wherein at least two scanning optical systems are disposed, at least one of the systems is used for obtaining an image, and the other is used for the correlation analysis.

The invention is not limited to the embodiments only, but proper changes can be made without changing the scope.

For example, an activity degree of a biomolecule may be analyzed by obtaining measurement data regarding brightness or luminance from a measuring point in addition to a light intensity. A change in an optical polarization degree or resonance energy may be measured based on a principle of detecting a single molecule. By improving the analysis means to select a proper equation from different operational equations and to execute analysis according to component properties in portions designated as measuring points on the sample, accurate analyzing results may be obtained by dealing with various physical environments such as many types of biological samples in the cell or derived from different sources. In this case, it is advised that by storing a proper operational equation in the memory for each sample surface and/or each internal component to which a point to be designated on the image belongs beforehand, a proper operational equation is read according to an actually designated point to execute analysis.

Additionally, for example, the embodiments have been described by taking the example of measurement which uses the fluorescent correlation spectroscopy, but the invention is not limited to such spectroscopy. In other words, the invention can be applied to optional very small optical measurement which measures various optical characteristics (polarization, scattering, electrochemical emission, resonance energy transfer, plasmon resonance, and the like) by limiting a measuring target to a specific portion or area of the sample. The two-dimensional or three-dimensional image obtained for the sample is not limited to one static image, but may be a plurality of static images or video images sequentially updated in real time. Accordingly, based on the latest updated sample images, an optional number of measuring points can be designated by a desired timing. If the designated number is larger than that of simultaneous measurement, by making designation to group measuring points in desired combination, it is possible to execute simultaneous measurement at a plurality of points by a group unit. For example, points of different places to be simultaneously compared are preferably classified into the same group. According to the invention, depending on a type of very small optical measurement, designing is preferably made to optimize an amount of an applied light for obtaining an image and an amount of an applied light for detection. For example, according to the above mentioned fluorescent correlation spectroscopy, since a laser is applied continuously for a given time to measure a fluctuation in light intensity, a laser output weaker compared with an instantaneous scanning laser for obtaining an image is preferably set. In an example in which measuring points can be set by independent scanning systems, according to optical characteristics of measured portions or measured items at a plurality of measuring points, an optional timing or an irradiation time can be set to obtain optimal measuring results, or an output from the laser beam source can be varied from measuring point to point. The fluorescent dye has been used as an index material to obtain an optical signal. However, a fusion protein (green fluorescent protein, yellow fluorescent protein or the like), a chemical emission material, a magnetic material or the like may be used. Furthermore, for the sample holding means, any type can be used as long as it can hold a proper volume of cells or other optional materials under conditions for maintaining natural conditions.

According to the present invention, it is possible to provide a biomolecule analyzer which can capture various movements or changes of a target sample.

That is, according to the invention, information regarding dynamic behaviors of biomolecules, the number thereof or the like, and a correlation between desired different molecules can be obtained while target molecules of a plurality of very small areas discretely present in a cell are observed by a microscope observation and recorded. Thus, it is possible to capture and analyze various life activities such as signal transmission in a cell, material transfer, and cell division in real time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biomolecule analyzer which analyzes dynamic behaviors of biomolecules, comprising:

image obtaining means for obtaining an image corresponding to at least one observation area of a biological sample containing biomolecules held in a measurable state;

designation means for designating an arbitrary point on the image obtained by the image obtaining means;

arrangement means for arranging a measuring point in a point position on the sample corresponding to the point designated by the designation means so that the measuring point may continuously coincide with the point position;

measurement means for measuring a signal derived from dynamic information of an object to be measured from the measuring point arranged by the arrangement means; and analysis means for analyzing measuring results of the measurement means.

2. The biomolecule analyzer according to claim 1, wherein:

the image obtained by the image obtaining means contains a three-dimensional area; and the arrangement means arranges the measuring point on an arbitrary three-dimensional point.

3. The biomolecule analyzer according to claim 1, wherein:
the measurement means obtains a plurality of signals different in time from the same measuring point, and
the analysis means compares outputs between the measuring points, and executes an operation.

4. The biomolecule analyzer according to claim 1, wherein the measurement means measures an intensity of an optical signal.

5. The biomolecule analyzer according to claim 1, wherein the analysis means executes the operation by using proper operational equations regarding dynamic information according to components on the sample to which the designated point belongs.

6. The biomolecule analyzer according to claim 1, wherein:
the designation means is configured to designate two or more arbitrary points, the arrangement means and the measurement means independently function at the two or more designated points, and
the analysis means outputs measuring results obtained from the two or more points to be compared.

* * * * *